United States Patent

Ishida

Patent Number: 5,885,508
Date of Patent: Mar. 23, 1999

[54] CATHETER TUBE AND A METHOD OF PROCESSING THE INNER SURFACE OF A TUBE

[75] Inventor: Toshinobu Ishida, Shinzuoka, Japan

[73] Assignee: Terumo Kabushiki Kaisha, Tokyo, Japan

[21] Appl. No.: 859,376

[22] Filed: May 20, 1997

Related U.S. Application Data

[62] Division of Ser. No. 499,191, Jul. 7, 1995, Pat. No. 5,681,296.

[30] Foreign Application Priority Data

Jul. 11, 1994 [JP] Japan .................................. 6-158957

[51] Int. Cl.⁶ .................................................. B29C 41/02
[52] U.S. Cl. .................. 264/313; 264/318; 425/DIG. 58
[58] Field of Search ........................... 264/313, 318, 264/209.2; 425/DIG. 58

[56] References Cited

U.S. PATENT DOCUMENTS

| | | | |
|---|---|---|---|
| 1,387,067 | 8/1921 | Murray | 264/313 |
| 1,596,754 | 8/1926 | Moschelle . | |
| 3,810,729 | 5/1974 | Patchell | 425/308 |
| 4,250,135 | 2/1981 | Orsini | 264/227 |
| 4,343,848 | 8/1982 | Leonard, Jr. | 428/156 |
| 4,615,359 | 10/1986 | Affa et al. . | |
| 4,876,837 | 10/1989 | Kelly et al. | 52/287 |
| 4,973,321 | 11/1990 | Michelson . | |
| 4,995,252 | 2/1991 | Robertson et al. | 72/194 |
| 5,244,619 | 9/1993 | Burnham . | |
| 5,266,257 | 11/1993 | Kildune | 264/313 |
| 5,496,292 | 3/1996 | Burnham . | |
| 5,564,214 | 10/1996 | Tsurufuji | 43/24 |

FOREIGN PATENT DOCUMENTS

| | | |
|---|---|---|
| 2 655 548 | 6/1991 | France . |
| 6-4300 | 1/1994 | Japan . |
| 6-4301 | 1/1994 | Japan . |

*Primary Examiner*—Jan H. Silbaugh
*Assistant Examiner*—Edmund H. Lee
*Attorney, Agent, or Firm*—Burns, Doane, Swecker & Mathis, LLP

[57] ABSTRACT

Catheter tube 2 has a multiple of small bead-like projections 21 formed on the inner surface. The inner surface of the tube 2 comprises projections 21 and flat areas 22. A guide wire inserted into the lumen 5 of the tube 2 contacts its inner surface only at the projections 21. The catheter tube 2 has the inner surface embossed in such a way that the guide wire can be manipulated with high efficiency even if the diameter of the tube is very small.

7 Claims, 3 Drawing Sheets

CATHETER TUBE AND A METHOD OF PROCESSING THE INNER SURFACE OF A TUBE

This application is a divisional of application Ser. No. 08/499,191 filed Jul. 7, 1995, now U.S. Pat. No. 5,681,296.

BACKGROUND OF THE INVENTION

This invention relates to a method of forming a multiple of small projections on the inner surface of comparatively small-diameter catheter tubes such as those in balloon dilatation catheters and cerebrovascular treating catheters. The invention also relates to comparatively small-diameter catheter tubes having a multiple of small projections formed on the inner surface.

One of the methods commonly adopted today in the treatment of myocardial infarction and angina pectoris is percutaneous transluminal coronary angioplasy (PTCA), in which a dilatation catheter fitted with a balloon at an end is used to dilate the lesion (the area of stenosis) in a coronary artery, thereby improving the distal blood circulation. The balloon catheter used in PTCA comprises basically a shaft as the main body, a dilatation balloon fitted near the distal end of the shaft and a hub fitted at the proximal end of the shaft. The shaft as the main body has a first lumen that connects the hub to the balloon for inflating it with a pressurized fluid and a second lumen that extends beyond the hub and the balloon to the distal end of the catheter and through which a guide wire is to be passed.

Since the shaft needs at least two lumens having those capabilities, it is common practice to employ either a plastic tube having a multi-hole cross section such as a double-lumen tube or a coaxial shaft consisting of an inner and an outer tube. The inner tube of the coaxial shaft has a smooth inner surface as produced by either a common tubing method or an wire coating method.

With the recent expansion of the application of PTCA, an effort is being made to reduce the diameter of PTCA dilatation catheters. The ultimate purpose of this effort is to enable application to further distal lesion of the coronary artery or to reduce the invasion and, to this end, it is necessary to employ even finer guiding catheters. At the early stage of the development of PTCA, dilatation catheters had shaft sizes of at least 4 Fr (1.33 mm) but today most of them are 3 Fr (1 mm) and less. This is also true with guiding catheters, which are typically 9 Fr (3 mm), sometimes 6 Fr (2 mm), in size. Accordingly, the lumen of the dilatation catheter for the passage of the guide wire has become thinner and the resulting decrease in the clearance between the guide wire and the lumen has caused the problem of lower steerability.

Another class of small-diameter catheters are catheters for use in cerebrovascular embolization which is typically applied to aneurysms and arterio-venous malformation. With their distal end inserted to either the lesion in the brain or a nearby area, a liquid embolic substance such as a cyanoacrylate or a dimethyl sulfoxide solution of ethylene-vinyl alcohol copolymer, or a particulate embolic substance such as a polyvinyl alcohol granule or an embolic coil is injected into a vessel through the inserted distal end. Such catheters are also required to have a sufficient fineness to insure smooth insertion into vessels in the brain that are very thin and which have many bends and bifurcations.

As is generally known, the problem of reduced steerability of the guide wire through small-diameter catheters can be solved by reducing the contact area and, hence, the frictional resistance. It is thus anticipated that if the inner surface of the lumen of a dilation catheter for the passage of a guide wire is made sufficiently irregular to reduce the area of contact with the guide wire, the frictional resistance of the inner surface is reduced and, hence, the steerability of the guide wire is improved.

Two conventional methods for embossing the surface of a tube during extrusion molding are by cooling the lip of an extrusion die which is near the exit of resin and by performing extrusion with a profiled die.

Methods are also known that form small asperties on the inner surface of a tube. See, for example, JPB 89/16653 which teaches a method of extrusion molding a thermoplastic resin as the inner mold in the channel of a molten resin is vibrated to form asperities on the surface of the resin that is in contact with the inner mold. JPB 94/4301 teaches a method that comprises applying a coating of a silicone resin and an inorganic powder to the surface of a metal wire, baking the applied coating to form a primary film, then applying a tube forming resin, baking it, subsequently stretching the metal wire to an extent that does not exceed the yield point, thereby separating the tube from the primary film that has small asperities formed on the inner surface.

The method of embossing the tube surface by cooling the lip is applied extensively to the outer surface of tubes but not to the inner surface; from the structural viewpoint of the die, this method is very difficult to perform efficiently on small-diameter tubes and its use is limited to certain cases of inflation molding with a large die.

The other embossing technique which relies upon molding with a profiled die is only capable of forming ridges as strips and does not allow for molding by the wire coating method (i.e., a thin metal core is moved lengthwise as a resin is extruded through a small-bore die to cover the metal core successively); therefore, this method does not guarantee sufficient dimensional stability to enable the formation of a small-diameter tube.

The method disclosed in JPB 89/16653 requires large equipment to vibrate the inner mold and, in addition, controlling the stroke of vibrating the inner mold and the speed of extrusion in such a way as to form small asperities is very difficult to achieve. Furthermore, if a small-diameter tube is to be formed, the vibrating inner mold tends to cause unevenness in the wall thickness and other defects that will impair the dimensional stability of the part being molded.

The method described in JPB 94/4301 also has a problem in that the particles of inorganic powder shed off the metal wire during production to cause uneven asperties or remain within the lumen of the tube to potentially affect the patient when the catheter tube as the final product is inserted into his body. What should additionally be noted is that the tube formed by the method under consideration overlies the high points created by the particles of the inorganic powder on the surface of the metal wire; therefore, the tube produced is of such a structure that small recesses are formed in the generally flat inner surface. Since the guide wire will contact the generally flat areas of the inner surface of the tube, the frictional resistance developing on the guide wire will not be reduced by a satisfactory amount.

Under the circumstances, there are not available any catheter tubes that have small inside diameters not more than about 1 mm and that are embossed on the inner surface to such an extent that the frictional resistance on a guide wire can be reduced significantly.

SUMMARY OF THE INVENTION

An object, therefore, of the invention is to provide a catheter tube of a comparatively small diameter that has multiple of small asperities formed on the inner surface.

Another object of the invention is to provide a method of processing the inner surface of a tube by which a multiple of small asperities can be formed on the inner surface of a tube of a comparatively small diameter.

The first object of the invention can generally be attained by:

(1) a catheter tube having a multiple of small projections formed on the inner surface, said inner surface consisting of small bead-like projections and generally flat areas other than said projections, and said projections and said flat areas being formed of the same material in a unitary assembly; and (2) a catheter as recited under (1), which is a medical tube having an inside diameter of 1 mm or less.

Preferably, a catheter tube is provided, wherein said small bead-like projections are generally rectangles having an average size 0.1–0.8 mm in length and 0.03–0.3 mm in width or ellipses having an average diameter of 0.05–0.4 mm, the average distance between projections is 5 mm or less than 5 mm, and the average height of projections is 0.002–0.03 mm.

Preferably, a catheter tube is provided, wherein the total area ratio of said bead-like projections is 0.01–0.2 and the total area ratio of said generally flat areas is 0.8–0.99.

Preferably, a catheter tube is provided, wherein the average number of said bead-like projections is 50–1000 /cm$^2$, the average distance between the projections is 5 mm or less than 5 mm, and the average height of the projections is 0.002–0.03 mm.

Preferably, a catheter tube is provided, wherein said small bead-like projections are long narrow pieces inclined or right angled to the longitudinal axis of the catheter tube.

When the catheter tube, which have the small bead-like projections being long narrow pieces inclined or right angled to the longitudinal axis of the catheter tube, is bended, it is hardly kinked.

The second object of the invention can generally be attained by:

(3) a method of processing the inner surface of a tube to form a multiple of small projections on the inner surface, in which a metal core that has been embossed to form a multiple of small recesses in the outer surface is coated with a molded synthetic resin material and subsequently extracted;

(4) a method as recited under (3), wherein said metal core is a copper wire; and (5) a method as recited under (3) or (4), wherein said metal core is knurled to have a multiple of small recesses formed in the outer surface.

DETAILED DESCRIPTION OF THE INVENTION

The present invention will now be described in detail.

Figure 1:
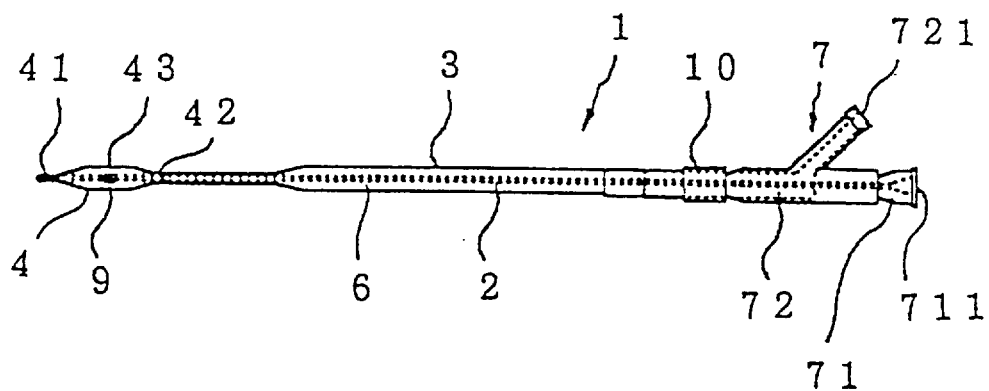
FIG. 1 is a plan view of a catheter tube according to an embodiment of the invention.
Figure 2:
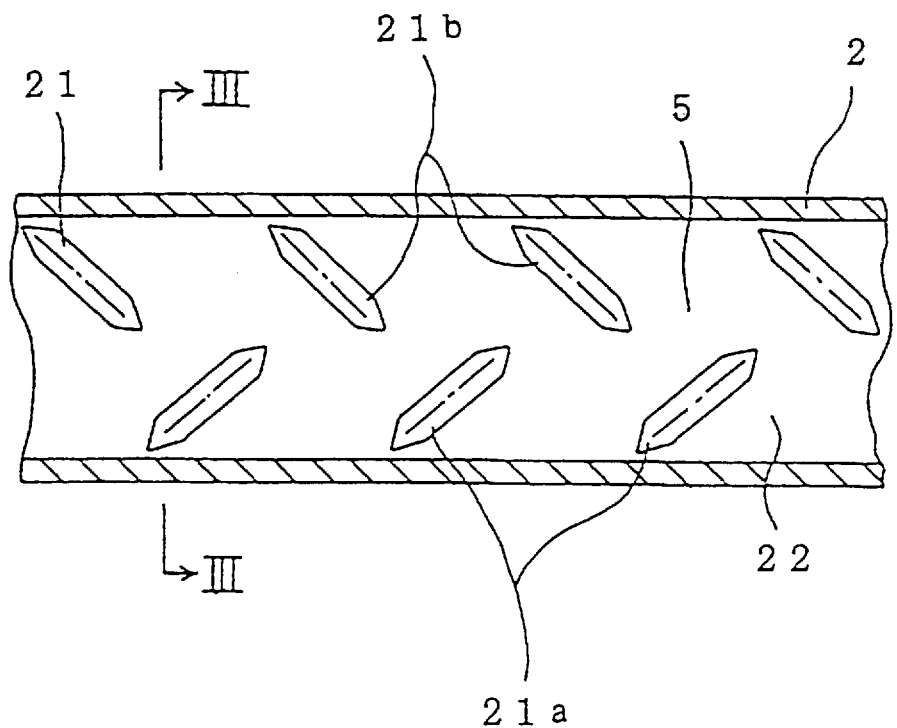
FIG. 2 is a longitudinal section showing, partly enlarged, the catheter tube of FIG. 1.
Figure 3:
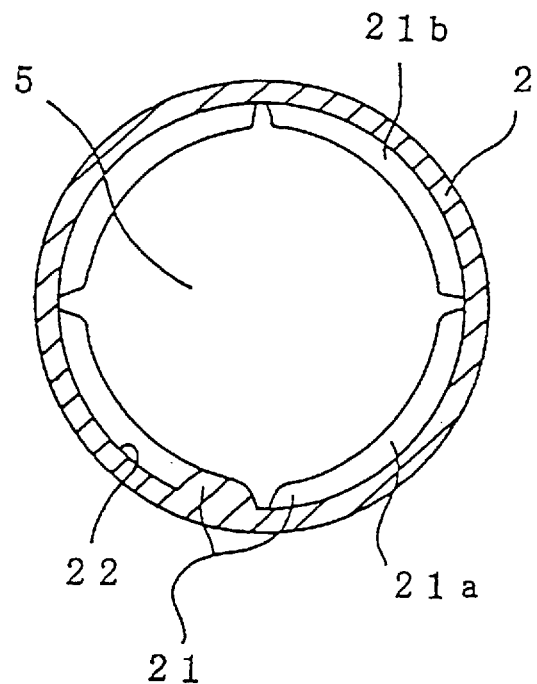
FIG. 3 is a cross section taken on line III—III of FIG. 2.

FIG. 1 is a plan view of a catheter tube according to an embodiment of the invention; FIG. 2 is a longitudinal section showing, partly enlarged, the catheter tube of FIG. 1; and FIG. 3 is a cross section taken on line III—III of FIG. 2.

The catheter tube of the invention which is indicated by 1 in FIG. 1 has a multiple of small projections formed on the inner surface and is characterized in that said inner surface consists of small bead-like projections 21 and generally flat areas 22 other than the projections 21, and that the projections 21 and the generally flat areas 22 are formed of the same material in a unitary assembly.

The catheter tube will now be described with reference to FIGS. 1–3. The catheter tube 1 shown in FIG. 1 is a balloon catheter for use in PTCA and consists of a main body having an inner tube 2 and an outer tube 3, and a bifurcate hub 7. Inner tube 2 has a lumen 5 that is open at the distal end. Lumen 5 provides a passageway through which a guide wire can be inserted and it communicates with a first opening 711 that forms a guide wire port on the bifurcate hub 7. Outer tube 3 has inner tube 2 inserted thereinto and it is provided coaxially with the inner tube 2 in a position backward of the distal end of the inner tube 2 by a specified length. A lumen 6 is formed between the inner surface of the outer tube 3 and the outer surface of the inner tube 2. The thus formed lumen 6 of the outer tube 3 has an adequate capacity. Lumen 6 communicates at the basal end to a second opening 721 which serves as an injection port on the bifurcate hub 7 through which a fluid (e.g. a radiopaque agent for angiography) is injected to inflate balloon 4.

Balloon 4 comprises a distal end portion 41, a basal end portion 42, and a generally cylindrical portion 43 in the middle. The basal end portion 42 is attached to the outer tube 3 and the balloon 4 communicates with the lumen 6 in an area near the basal end portion in such a way that it can be contracted or folded back as required. Stated more specifically, balloon 4 communicates with the distal end of the lumen 6 in an area near the basal end portion of the balloon 4. Thus, lumen 6 having a comparatively large capacity is provided in such a way as to communicate with the basal end of the balloon 4 and this allows an inflating fluid to be injected easily from the lumen 6 into the balloon 4.

The outer surface of the inner tube 2 is provided with a marker 9 made of an X-ray opaque material (e.g. gold, platinum or alloys thereof) in a position intermediate between the distal end portion 41 and the basal end portion 42. Marker 9 is provided to insure that the position of balloon 4 can easily be identified under examination with X-rays. In a preferred embodiment, the marker 9 is a ring that is formed of gold or platinum or alloys thereof and that is clamped onto the outer surface of the inner tube 2. This arrangement ensures the production of a distinct X-ray angiogram.

Bifurcate hub 7 consists of a hub 71 secured to the inner tube 2 that has the first opening 711 which communicates with the lumen 5 to form the guide wire port and a hub 72 secured to the outer tube 3 that has the second opening 721 which communicates with the lumen 6 to form the injection port. The two hub members are secured to each other.

In the case shown, a reinforcing tube 10 is fitted around the outer tube 3 in an area near its basal end. The reinforcing tube 10 may typically be formed of a heat-shrinkable material in such a way that after heat shrinkage, the inside diameter of the tube 10 will be slightly smaller than the outside diameter of the outer tube 3 near the basal end; the tube can easily be installed on the outer tube 3 by slipping it over the outer tube 3 to an area near the basal end of the latter and heating it (by, for example, blowing hot air) so that it shrinks. The reinforcing tube is in no way limited to the embodiment just described above and a tube similar to the reinforcing tube 10 may also be fitted on the inner tube 2.

As shown in FIGS. 2 and 3, the inner surface of the inner tube 2 consists of a multiple of small bead-like projections 21 and generally flat areas 22 other than the projections 21. Because of this arrangement, a guide wire inserted into the lumen 5 of the inner tube 2 will contact the inner surface of the inner tube at the bead-like projections 21 but not in the generally flat areas 22. Since the projections 21 are bead-like, the area of contact between the inner surface of the inner tube 2 and the guide wire is sufficiently small (for example, the total area ratio of the flat areas based on the inner surface unit area (1 mm$^2$) of the catheter tube in 80–99%) to improve the steerability of the guide wire.

The projections 21 and the generally flat areas 22 are formed of the same material in a unitary assembly. Hence, the inner surface of the inner tube 2 has no joints between each of the projections 21 and the generally flat areas 22 and there is no chance for the projections 21 to shed off the inner surface of the inner tube 2.

The projections 21 are in the form of beads that extend at an angle with the length of the catheter tube. The projections 21 also consists of two groups, 21a and 21b, that are oblique in opposed directions. The projections 21 align in two rows along the length of the inner tube 2. In each row, all projections 21 are oblique in the same direction but in opposite direction to the projections in the adjacent row. In other words, the projections are formed in such a way that those in one row which are oblique in one direction alternate with those in the other row which are oblique in opposite direction. Additionally, a projection 21 in one row is positioned intermediate between two projections in the adjacent row so that the projections in one row alternate with those in the adjacent row.

Projections 21 extend preferably in a length of 0.1–0.8 mm, more preferably 0.3–0.6 mm, and preferably in a width of 0.03–0.3 mm, more preferably 0.05–0.15 mm. If two projections 21 are spaced apart by an unduly great distance, a guide wire will contact generally flat areas 22 other than projections 21 to produce increased frictional resistance. Hence, the spacing between projections 21 is preferably not greater than about 5 mm, more preferably between about 0.3 and 1.0 mm.

Figure 4:
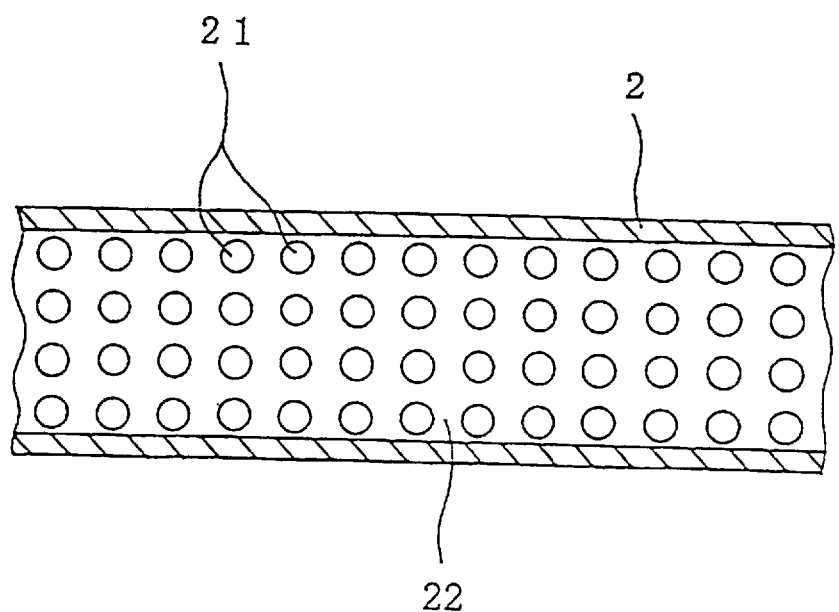
FIG. 4 is a longitudinal section showing, partly enlarged, a catheter tube according to another embodiment of the invention.

It should be noted here that the shape of projections 21 is in no way limited to what is shown in FIG. 2; they may be a grid pattern of small circular beads as shown in FIG. 4 or, alternatively, satin-like projections may be substituted. If the arrangement shown in FIG. 4 is to be adopted, circular projections 21 have preferably a diameter of about 0.05–0.4 mm, more preferably about 0.1–0.25 mm, and are spaced apart by a distance not exceeding 5 mm, more preferably about 0.3–1.0 mm.

The inner tube 2 is made of a resin material having a certain degree of flexibility, as exemplified by polyolefins such as polyethylene, polypropylene, ethylene-propylene copolymer, etc., mixtures thereof, olefinic copolymers such as an ethylene-vinyl acetate copolymer, etc., and thermoplastic resins such as polyvinyl chloride, polyamides, polyamide elastomers, etc. Polyolefins are preferred examples.

The inner tube 2 has an outside diameter that ranges preferably from about 0.4 to about 1.5 mm, more preferably from about 0.5 to about 0.8 mm, and an inside diameter that ranges preferably from about 0.25 to about 1.0 mm, more preferably from about 0.4 to 0.7 mm. Even if the inside diameter of the inner tube 2 is smaller than 1 mm, the projections 21 provided on its inner surface insures the good steerability of a guide wire.

The outer tube 3 is preferably made of a material having a certain degree of flexibility, as exemplified by polyolefins such as polyethylene, polypropylene, polybutene, ethylene-propylene copolymer, etc., mixtures thereof, crosslinked polyolefins produced by crosslinking those polyolefins or mixtures thereof, and thermoplastic resins such as polyamides, polyamide elastomers, etc. The last mentioned group of thermoplastic resins are preferred, and the polyolefins are more preferred.

The outer tube 3 has an outside diameter that ranges preferably from about 0.7 to about 2.0 mm, more preferably from about 0.9 to about 1.2 mm, and an inside diameter that ranges from about 0.5 to about 1.7 mm, more preferably from about 0.7 to about 1.0 mm.

The balloon 4 is preferably made of a material having a certain degree of flexibility, as exemplified by polyolefins such as polyethylene, polypropylene, polybutene, ethylene-propylene copolymer, etc., mixtures thereof, crosslinked polyolefins produced by crosslinking those polyolefins or mixtures thereof, olefinic copolymers such as an ethylene-vinyl acetate copolymer, etc., and thermoplastic resins such as polyethylene terephthalate, polyvinyl chloride, polyurethanes, polyphenylene sulfide, polyamides, polyamide elastomers, etc. The last mentioned group of thermoplastic resins are preferred and the crosslinked polyolefins are more preferred.

The balloon 4 has such dimensions that, when inflated, the generally cylindrical portion 43 has an outside diameter that ranges preferably from about 1.0 to about 5.0 mm, more preferably from about 1.5 to about 3.5 mm, and a length that ranges preferably from about 5.05 to about 50.0 mm, more preferably from about 10.0 to about 40.0 mm. The overall length of the balloon 4 is preferably from about 15 to about 60 mm, more preferably from about 20 to about 50 mm.

While the catheter of the present invention has been described above with particular reference to the embodiment shown in FIGS. 1–3, this is not the only case of the invention and various other embodiments may be adopted. For example, the inner tube 2 need not be formed of a single layer throughout but, instead, an inside layer including the inner surface comprising projections 21 and generally flat areas 22 may be coated with an outside layer composed of another material, thereby forming a two- or three-layered structure or multi-layered having more than three layers. If desired, part of the inner surface of the tube may solely consist of flat areas that are continuous to each other without being interrupted by projections 21.

The catheter tube of the invention is in no way limited to the above-described balloon catheter for use in PTCA but may be shaped to be adaptive for use in various other applications such as embolization, angiography, endoscopy, etc.

Figure 5:
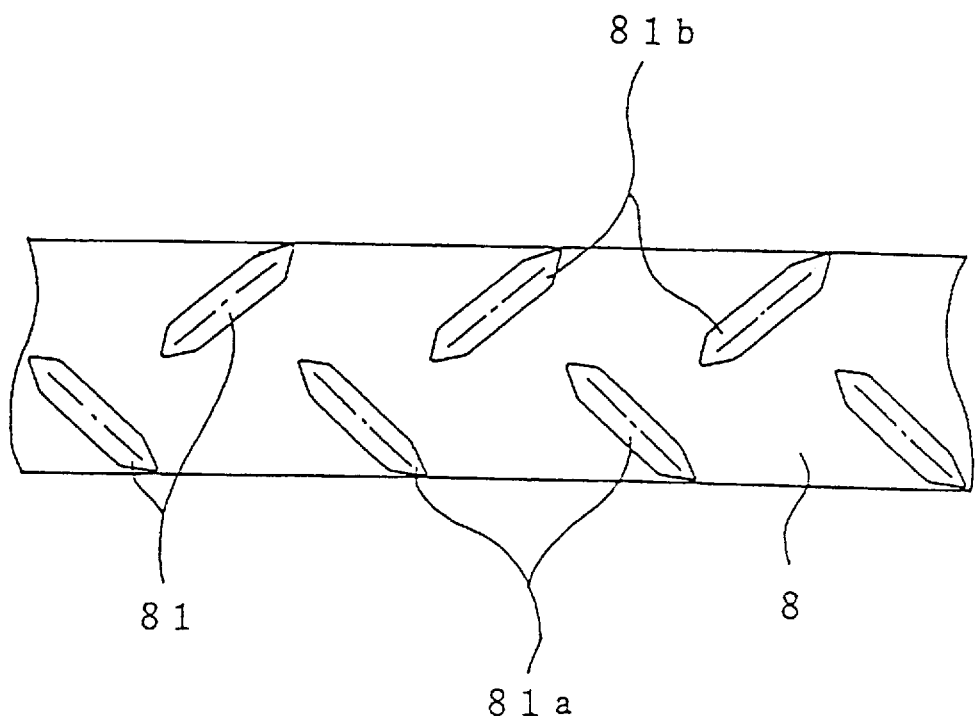
FIG. 5 is an enlarged view of the metal core for use in the method of invention for processing the inner surface of a tube.

The method of processing the inner surface of a tube according to the second aspect of the invention will now be described in detail with reference to the case of producing the catheter shown in FIGS. 1–3. FIG. 5 is an enlarged view of a metal core for use in-the processing method of the invention.

The method of the invention to process the inner surface of a tube is one-of forming a multiple of small projections on the inner surface, in which a metal core that has been embossed to form a multiple of small recesses in the outer surface is coated with a molded synthetic resin material and subsequently extracted.

This method will now be described with reference to FIG. 5.

The method starts with providing a metal core indicated by 8 in FIG. 5. The metal core 8 may be a metal wire typically made of copper, aluminum, gold, silver, stainless steel or the like. A copper wire is particularly referred since it is easy to process by the knurling method to be described below. The cross-sectional shape of the metal core 8 is not limited to a circle but may be a polygon such as a square or a hexagon or it may be elliptical.

The outer surface of the metal core 8 is preliminarily knurled to have a multiple of small recesses 81 formed as grooves that extend at an angle with the length of the metal core 8. The recesses 81 also consist of two groups, 81a and 81b, that are oblique in opposed directions. The recesses 81 align in two rows along the length of the metal core 8. In each row, all recesses 81 are oblique in the same direction but in opposite direction to the recesses in the adjacent row. In other words, the recesses are formed in such a way that those in one row which are oblique in one direction alternate with those in the other row which are oblique in opposite direction. Additionally, a recess 81 in one row is positioned intermediate between two recesses in the adjacent row so that the recesses in one row alternate with those in the adjacent row.

The shape of the recesses 81 is not limited to what is shown in FIG. 5 and they may be a grid pattern of circular concaves or, alternatively, satin-like concaves may be substituted.

The metal core 8 may be knurled on the outer surface by means of a roller having correspondingly shaped projections. Recesses 81 may be formed by methods other than knurling such as sand blasting, irradiation with laser light, the use of a mechanical file or some other means of removing selected areas of the outer surface of the metal core 8.

The recesses 81 have a depth that ranges preferably from about 0.003 to about 0.10 mm, more preferably from 0.005 to about 0.08 mm. The recesses 81 extend preferably in a length of from about 0.1 to about 0.8 mm, more preferably from about 0.3 to about 0.6 mm, and preferably in a width ranging from about 0.03 to about 0.3 mm, more preferably from about 0.05 to about 0.15 mm.

In the next step, the outer surface of the metal core 8 is coated with a molded synthetic resin material of which the tube is to be made. This can be achieved by extruding the synthetic resin onto the outer surface of the metal core 8 or by coating, dipping or some other suitable method. The wire coating method, in which a fine metal core is moved lengthwise as the resin is extruded through a small-bore die to cover the core metal successively, is preferably employed since it is capable of molding small-diameter tubes with good dimensional stability.

The tube thus formed over the outer surface of the metal core 8 has small projections formed on the inner surface by means of the recesses 81 in the outer surface of metal core 8 and the other areas of the inner surface of the tube are formed generally flat by means of the flat areas of the outer surface of the metal core 8 other than the recesses 81. The synthetic resin material to be used in molding the tube may be the same as what is used to form the inner tube 2.

Subsequently, the metal core 8 which is coated with the molded synthetic resin material is extracted to leave the molding in a tubular form. To extract the metal core 8, it is elongated to a smaller diameter so that the tube molding separates from the metal core 8. Thereafter, the metal core 8 may be extracted from the tube.

One way to elongate the metal core 8 is to fix an end of the metal core 8 of a specified length while the other end is simply pulled.

When separating and extracting the metal core 8 from the tube molding, the former may be elongated by an amount of about 10–30%, typically about 15–25%.

The process described above enables the production of inner tube 2 of the construction shown in FIGS. 2 and 3. This inner tube 2 is assembled with outer tube 3, balloon 4, inner tube hub 71 and outer tube hub 72 in an appropriate way to produce a balloon catheter of the construction shown in FIG. 1.

According to the method described above, one only need form recesses in a metal core in an extra step to the process of shaping an ordinary tube and by so doing, a tube can be simply produced which has an embossed inner surface comprising small projections and generally flat areas other than these projections, which projections and generally flat areas being formed of the same material in a unitary assembly. Since the metal core restricts the inside diameter of the tube, shaping can be accomplished with high dimensional stability and even tubes having inside diameters smaller than 1 mm can be shaped in a satisfactory manner. The method of the invention has the added advantage that by changing the shape and depth of recesses to be formed in the metal core, one can change appropriately the shape and height of the projections to be formed on the tube as the final product.

It should be mentioned that if the shape of the recesses to be formed in the metal core is selected appropriately, the method of the invention for processing the inner surface of a tube can also be applied to the manufacture of tubes the inner surface of which has asperities of shapes other than that shown in FIGS. 2 and 3.

The following examples are provided for the purpose of further illustrating the present invention but are in no way to be taken as limiting.

EXAMPLE 1

A copper wire having a diameter of 0.55 mm was knurled to form recesses in the outer surface as shown in FIG. 5, in which the wire and the recesses are indicated by numerals 8 and 81, respectively. High-density polyethylene (MITSUBISHI POLYETHY HD EY-40H of Mitsubishi Petrochemical Co., Ltd.) was molded around the copper wire 8 by a common wire coating technique to give an outside diameter of 0.70 mm. The recesses 81 had a depth of 0.02 mm, a length of 0.4 mm and a width of 0.1 mm. Two recesses 81 were spaced apart by 0.9 mm along the length of the copper wire 8.

Subsequently, the copper wire 8 and the resin molding over its outer surface were cut to a length of about 2 m. With an end of the copper wire 8 fixed, the other end was pulled to make the copper wire 8 thin enough to be subsequently extracted, thereby producing a tube of the construction shown in FIGS. 2 and 3, which had an inside diameter of 0.5 mm and an outside diameter of 0.7 mm, with the inner surface embossed to have projections 21 having 0.008 mm of the average height and generally flat areas 22 as the result of the transfer of the small recesses 81 in the outer surface of the copper wire 8.

EXAMPLE 2–8

Tubes having an inside diameter of 0.55 mm and an outside diameter of 0.70 mm were produced employing the same resin and forming conditions as in Example 1, except that the depth of recesses 81 was changed to 0.003 mm, 0.005 mm, 0.01 mm, 0.04 mm, 0.06 mm, 0.08 mm and 0.10 mm.

The thus obtained projections had the average height of 0.002 mm, 0.003 mm, 0.005 mm, 0.015 mm, 0.020 mm and 0.030 mm respectively, but the last one (used the depth of recess being 0.10 mm) could not measured the average height of the projections.

The total area ratio of the projections based on the inner surface unit area (1 mm$^2$) of the catheter tube, and the total number of the projections based on the inner surface unit area (1 cm$^2$) of the catheter tube can be calculated as follows;

| | |
|---|---|
| the area of one projection | 0.04 mm$^2$ |
| the number of projections in one unit portion | 4 |
| the inner surface area of the tube in one unit portion | 1.56 mm$^2$ |
| 0.04 × 4 /1.56 = 0.1 mm$^2$/mm$^2$ | |
| (4/1.56) × 100 = 257.2 (1/cm$^2$) | |

COMPARATIVE EXAMPLE 1

A tube having an inside diameter of 0.55 mm and an outside diameter of 0.70 mm was produced employing the same resin and forming conditions as in Example 1, except that the metal core was a solid (unknurled) copper wire having a diameter of 0.55 mm.

EXPERIMENT

The high-density polyethylene tubes of Examples 1–8 and Comparative Example 1 were each cut to a length of 1.3 m and a PTCA guide wire (Hiper Flex of C.R. BARD Corp.; 0.36 mmφ) was inserted into each tube to such an extent that the tip came out of the distal end of the tube by a length of about 1 cm.

Subsequently, each tube and guide wire combination was inserted, with the tip of the guide wire entering first, into a loop (19 cmφ) of a high-density polyethylene tube having an inside diameter of 2.5 mm and an outside diameter of 4.0 mm. The insertion of the guide wire was continued until it became no longer movable back and forth. The length of guide wire insertion to that point was measured.

With the tube of Comparative Example 1 which was produced by coating on the unknurled copper wire, the guide wire was no longer movable when it was inserted by a length of 80 cm. On the other hand, with the tube of Example 1 having an embossed inner surface, the guide wire was easily movable even when it was inserted by a length of 130 cm.

The situation was the same with the tubes of Examples 2–7 and the guide wire could be moved even when it was inserted by a length of 130 cm. However, the tube of Example 2 which was produced using a copper wire 8 having recesses 81 formed to a depth of 0.003 mm presented more resistance to the movement of the guide wire than the tubes of Examples 3–7 which were produced using copper wires having recesses 81 formed to depths of 0.005–0.08 mm. The tube of Example 8 which was produced using a copper wire having recesses 81 formed to a depth of 0.10 mm experienced so much difficulty in extracting the copper wire 8 that it elongated or otherwise deform.

As described on the foregoing pages, the catheter tube according to the first aspect of the invention has a multiple of small projections formed on the inner surface and it is characterized in that said inner surface comprises the small bead-like projections and generally flat areas other than said projections and that said projections and said generally flat areas are formed of the same material in a unitary assembly. Having these features, the catheter of the invention is available in a small diameter and yet permits a guide wire to be manipulated efficiently.

The method of processing the inner surface of a tube according to the second aspect of the invention is intended to form a multiple of small projections on the tube's inner surface and it is characterized in that a metal core embossed to have a multiple of small recesses formed in the outer surface is coated with a molded synthetic resin material and subsequently extracted to leave the resin molding in a tubular form. Having these features, the method enables even a small-diameter tube which permits a guide wire to be manipulated efficiency to be shaped easily and with high dimensional stability.

What is claimed is:

1. A method of forming multiple small projections on an inner surface of a tube having an inner diameter of 1 mm or less, comprising coating a metal core having an outer surface on which has been directly embossed multiple small recesses in the outer surface with a synthetic resin material to form a tube on the outer surface of the metal core having multiple small projections produced by the multiple small recesses on the outer surface of the metal core, elongating the metal core to a smaller diameter so that the tube separates from the core, and extracting the elongated metal core from the tube having an inner diameter of 1 mm or less.

2. A method according to claim 1, wherein said metal core is a copper wire.

3. A method according to claim 1, wherein said metal core is knurled to form the multiple small recesses in the outer surface of the metal core.

4. A method of producing a catheter tube having an inner diameter of 1 mm or less comprising:

applying a synthetic resin coating on an outer surface of a metal core to form a tube on the outer surface of the metal core, the outer surface of the metal core being provided with a plurality of spaced apart recesses and the tube being formed directly on the outer surface of the metal core to produce a plurality of inwardly extending spaced apart projections on the tube formed by the synthetic resin filling the recesses in the outer surface of the metal core;

elongating the metal core to reduce the diameter of the metal core so that the tube separates from the metal core;

extracting the elongated metal core from the tube to produce the catheter tube having an inner surface from which extends the plurality of projections.

5. A method according to claim 4, wherein the recesses in the outer surface of the metal core are in the form of grooves that each extend at an angle with respect to a lengthwise direction of the metal core.

6. A method according to claim 4, wherein the recesses in the outer surface of the metal core are arranged in rows.

7. A method according to claim 4, wherein the recesses in the outer surface of the metal core are completely surrounded by flat areas of the outer surface of the metal core.

* * * * *

UNITED STATES PATENT AND TRADEMARK OFFICE
CERTIFICATE OF CORRECTION

PATENT NO. : 5,885,508
DATED : March 23, 1999
INVENTOR(S) : Toshinobu Ishida

It is certified that error appears in the above-indentified patent and that said Letters Patent is hereby corrected as shown below:

On the title page: Item [54] and Column 1, line 3, title should read
-- METHOD OF PROCESSING THE INNER SURFACE OF A TUBE--.

In column 6, line 29, delete "5.00" to read -- 5.0--.

In column 7, line 2, delete "referred" and insert --preferred--.

In column 8, line 65, delete "recesses" and insert --recess--.

In column 10, line 51, delete "extends" and insert --extend--.

Signed and Sealed this

Ninth Day of November, 1999

Attest:

Q. TODD DICKINSON

*Attesting Officer*   *Acting Commissioner of Patents and Trademarks*